US012070020B2

(12) United States Patent
Farmer et al.

(10) Patent No.: US 12,070,020 B2
(45) Date of Patent: Aug. 27, 2024

(54) COMPOSITIONS AND METHODS FOR ENHANCED AQUATIC FARMING AND AQUARIUM FISH HUSBANDRY

(71) Applicant: Locus Solutions IPCo, LLC, Solon, OH (US)

(72) Inventors: Sean Farmer, North Miami Beach, FL (US); Ken Alibek, Solon, OH (US); Kent Adams, Twinsburg, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 273 days.

(21) Appl. No.: 16/498,101

(22) PCT Filed: Apr. 19, 2018

(86) PCT No.: PCT/US2018/028330
§ 371 (c)(1),
(2) Date: Sep. 26, 2019

(87) PCT Pub. No.: WO2018/195296
PCT Pub. Date: Oct. 25, 2018

(65) Prior Publication Data
US 2021/0112787 A1     Apr. 22, 2021

Related U.S. Application Data

(60) Provisional application No. 62/487,676, filed on Apr. 20, 2017.

(51) Int. Cl.
| A01K 61/80 | (2017.01) |
| A01K 61/13 | (2017.01) |
| A01K 63/04 | (2006.01) |
| A01N 37/00 | (2006.01) |
| A01N 63/32 | (2020.01) |
| A23K 10/10 | (2016.01) |
| A23K 10/16 | (2016.01) |
| A23K 10/18 | (2016.01) |
| A23K 50/80 | (2016.01) |
| A61K 36/06 | (2006.01) |
| A61K 38/06 | (2006.01) |
| A61P 3/02 | (2006.01) |
| C02F 103/20 | (2006.01) |

(52) U.S. Cl.
CPC ............ *A01K 61/80* (2017.01); *A01K 61/13* (2017.01); *A01K 63/04* (2013.01); *A01N 37/00* (2013.01); *A01N 63/32* (2020.01); *A23K 10/10* (2016.05); *A23K 10/16* (2016.05); *A23K 10/18* (2016.05); *A23K 50/80* (2016.05); *A61K 38/06* (2013.01); *A61P 3/02* (2018.01); *A01K 2227/40* (2013.01); *C02F 2103/20* (2013.01)

(58) Field of Classification Search
None
See application file for complete search history.

(56) References Cited

U.S. PATENT DOCUMENTS

| 7,556,654 | B1 | 7/2009 | Nero | |
| 8,454,983 | B2 | 6/2013 | DeChant et al. | |
| 2005/0266036 | A1* | 12/2005 | Awada | A01N 63/20 |
| | | | | 504/117 |
| 2010/0254957 | A1 | 10/2010 | Hua | |
| 2011/0044972 | A1 | 2/2011 | Fieldhouse et al. | |
| 2011/0237531 | A1 | 9/2011 | Yanagisawa et al. | |
| 2012/0039853 | A1 | 2/2012 | Corveleyn et al. | |
| 2012/0058895 | A1 | 3/2012 | Awada et al. | |
| 2012/0207912 | A1 | 8/2012 | Nichols et al. | |
| 2012/0220464 | A1 | 8/2012 | Giessler-Blank et al. | |
| 2013/0324406 | A1 | 12/2013 | Chisholm et al. | |
| 2015/0037302 | A1 | 2/2015 | Bralkowski et al. | |
| 2015/0044356 | A1 | 2/2015 | Bootsma et al. | |
| 2015/0045290 | A1 | 2/2015 | Coutte et al. | |
| 2015/0118203 | A1 | 4/2015 | Boyette et al. | |
| 2016/0083757 | A1 | 3/2016 | Fonesca et al. | |
| 2016/0168612 | A1* | 6/2016 | Soetaert | C12P 19/12 |
| | | | | 435/74 |
| 2016/0183556 | A1 | 6/2016 | Lu et al. | |

(Continued)

FOREIGN PATENT DOCUMENTS

| CN | 1847166 A | * 10/2006 |
| CN | 102696895 A | 10/2012 |

(Continued)

OTHER PUBLICATIONS

Price, N.P.J. et al. 2012. Structural characterization of novel sophorolipid biosurfactants from a newly identified species of *Candida* yeast. Carbohydrate Research 348: 33-41; specif. pp. 33, 36.*

Queensland Govt. Guidelines for constructing and maintaining aquaculture containment structures. Copyright 2007. The State of Queensland, Dept. of Primary Industries and Fisheries, pp. 1-40; specif. p. 15.*

Dusane, D.H. et al. 2010. Rhamnolipid mediated disruption of marine Bacillus pumilus biofilms. Colloids and Surfaces B: Biointerfaces 81: 242-248; specif. pp. 242, 243, 244, 246.*

EngMT-Sun, X.-X. et al. A method for treating red tide of seawater and freshwater algal bloom. Chinese Patent Application Publication No. CN1847166A; Date Published: Oct. 18, 2016. pp. 1-4; specif. pp. 1, 3.*

DeGraeve, M. et al. 2018. *Starmerella bombicola*, an industrially relevant, yet fundamentally underexplored yeast. FEMS Yeast Research 18: pp. 1-13; specif. p. 2.*

(Continued)

Primary Examiner — Adam Weidner
Assistant Examiner — Sharon M. Papciak
(74) Attorney, Agent, or Firm — SALIWANCHIK, LLOYD & EISENSCHENK

(57) ABSTRACT

The subject invention provides microbe-based products, as well as their use, for enhancing aquaculture. In particular, the subject invention provides materials and methods for producing healthy and high quality farmed fish by applying yeast and/or bio surfactant-based compositions to a fish farm. In one embodiment, the subject invention improves the environment in which the fish are farmed. In another embodiment, the subject invention provides a highly nutritious fish feed, as well as methods of feeding fish at low cost.

3 Claims, No Drawings

(56) References Cited

U.S. PATENT DOCUMENTS

| | | | |
|---|---|---|---|
| 2016/0298150 A1 | 10/2016 | Hirano et al. | |
| 2016/0374364 A1 | 12/2016 | Lee | |
| 2020/0329710 A1 | 10/2020 | Farmer et al. | |

FOREIGN PATENT DOCUMENTS

| | | | |
|---|---|---|---|
| CN | 103304043 A | 9/2013 | |
| EP | 0540074 A1 | 5/1993 | |
| EP | 2074889 A1 | 7/2009 | |
| JP | 2003009896 A | 1/2003 | |
| JP | 2008501039 A | 1/2008 | |
| JP | 2008173070 A | 7/2008 | |
| JP | WO2010050413 A1 | 5/2010 | |
| JP | 5622190 B2 | 11/2014 | |
| JP | 2015119698 A | 7/2015 | |
| WO | 2005117929 A1 | 12/2005 | |
| WO | 2007128766 A1 | 11/2007 | |
| WO | 2008002231 A1 | 1/2008 | |
| WO | 2011008570 A2 | 1/2011 | |
| WO | 2011114290 A1 | 9/2011 | |
| WO | 2017044953 A1 | 3/2017 | |
| WO | 2018049182 A2 | 3/2018 | |
| WO | 2018129299 A1 | 7/2018 | |

OTHER PUBLICATIONS

Faria, N.T. et al. 2014. Production of glycolipid biosurfactants, mannosylerythritol lipids, from pentoses and D-glucose/D-xylose mixtures by Pseudozyma yeast strains. Process Biochemistry 49: 1790-1799; specif. pp. 1790, 1791, 1792, 1793.*

Soberon-Chavez, G. et al. Biosurfactants: a general review. In: Biosurfactants, From Genes to Applications; Ed.: G. Soberon-Chavez. Copyright 2011 Springer Verlag Berlin Heidelberg. pp. 1-11; specif. pp. specif. pp. 2, 3, 5.*

Mazumder, A. et al. 1990. Effects of fish and plankton on lake temperature and mixing depth. Science 247: 312-315; specif. pp. 312 , 314.*

Markus, H. et al. 2010. What's that green stuff? Minnesota Conservation Volunteer, July-August, pp. 46-49; specif. p. 46.*

Hansen, M.H. et al. 1978. Mechanisms of hydrogen sulfide release from coastal marine sediments to the atmosphere. Limnology and Oceanography 23(1): 68-76; specif. pp. 68, 69 (Year: 1978).*

Wang, C. et al. 2011. Acute toxicity of live an decomposing green alga Ulva (Enteromorpha) prolifera to abalone Haliotis discus hannai. Chinese Journal of Oceanology and Limnology 29(3): 541-546; specif. pp. 541, 542, 544, 545 (Year: 2011).*

Martin, A.M., et al, "Production of Candida utilis Biomass as Aquaculture Feed." Journal of the Science of Food and Agriculture, 1993, 61(3): 363-370.

De Brito, D., Biosurfactants from renewable raw materials, Universidade do Minho Departamento de Engenharia Biológica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Kurtzman, C.P., et al., "Production of sophorolipid biosurfactants by multiple species of the Starmerella (Candida) bombicolayeast clade." FEMS Microbiol Lett, 2010, 311: 140-146.

Mikulski, D., et al., "Evaluation of phytic acid utilization by S. cerevisiae strains used in fermentation processes and biomass production." Journal of Basic Microbiology, 2017, 57: 87-91.

Morikawa, M., "Beneficial Biofilm Formation by Industrial Bacteria Bacillus subtilis and Related Species." Journal of Bioscience and Bioengineering, 2006, 101(1): 1-8.

Nitschke, M., et al., "Production and properties of a surfactant obtained from Bacillus subtilis grown on cassava wastewater." Bioresource Technology, 2006, 97: 336-341.

Sharma, A. et al., "A study on biosurfactant production in Lactobacillus and Bacillus sp." Int. J. Curr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Souza, K.S.T., et al., "New glycolipid biosurfactants produced by the yeast strain Wickerhamomyces anomalus CCMA 0358." Colloids and Surfaces B: Biointerfaces, 2017, 154: 373-382.

Andrade Silva, N.R., et al., "Biosurfactant-and-Bioemulsifier Produced by a Promising Cunninghamella echinulata Isolated from Caatinga Soil in the Northeast of Brazil." Int. J. Mol. Sci., 2014, 15: 15377-15395.

Luft, L., et al. "An overview of fungal biopolymers: bioemulsifiers and biosurfactants compounds production." Critical reviews in biotechnology 40.8 (2020): 1059-1080.

* cited by examiner

COMPOSITIONS AND METHODS FOR ENHANCED AQUATIC FARMING AND AQUARIUM FISH HUSBANDRY

CROSS-REFERENCE TO RELATED APPLICATION

This application is a National Stage Application of International Application No. PCT/US2018/028330, filed Apr. 19, 2018; which claims the benefit of U.S. provisional application Ser. No. 62/487,676, filed Apr. 20, 2017, both of which are incorporated herein by reference in their entirety.

BACKGROUND OF THE INVENTION

Aquaculture (aquafarming or aquatic farming) involves the cultivation of populations of freshwater or saltwater organisms under controlled conditions. More specifically, aquaculture is the farming of edible or ornamental fish and other aquatic organisms, such as shrimp and oysters. Cultivation of aquatic organisms typically involves enhancing production through some form of intervention in the rearing process, for example, regularly stocking a population, feeding a population, and/or protecting a population from predators. Global aquaculture operations have been reported to supply over half of the fish and shellfish that is consumed by humans.

Feeding a population of fish, especially in the case of large scale farming, comprises a large portion of aquaculture operating expenditures. Fish food must contain highly digestible protein sources along with a full range of other components required for proper nutrition, including amino acids, carbohydrates, vitamins, minerals, cholesterol and essential fatty acids. Feed sources can include, for example, fish meal, shrimp mix, squid meal, soybean meal, *Spirulina*, and whole wheat, or combinations thereof.

Some aquaculture methods include highly-sophisticated aquaponics that require multifaceted systems, which, in some cases, integrate fish farming with plant farming. Other methods, such as large-scale factory fish farming, operate under the goal of producing as many fish as possible, as cheaply as possible. Fish and shrimp can be kept in overcrowded conditions, so the risk of contamination is high, both within the enclosures themselves and in the surrounding waters. Fish factories can be unsanitary, and often require massive amounts of antibiotics, hormones, and pesticides to control the spread of disease.

Another issue facing aquaculture operations is a significant loss of fish product due to carbon dioxide "asphyxiation." The primary sources of carbon dioxide in fish ponds are derived from respiration by fish, as well as microscopic plants and animals that make up the pond biota. Decomposition of organic matter is also a major source of carbon dioxide. Increased levels of carbon dioxide in fish ponds leads to asphyxiation and death of fish, plus water from decomposing fish carcasses.

Current methods of carbon dioxide removal include chemical treatment of pond water with liming agents such as quicklime, hydrated lime or sodium carbonate. These agents react directly with carbon dioxide, resulting in reduced carbon dioxide and increased alkalinity. However, application of chemicals to treat excessive carbon dioxide only provides a temporary solution and is limited due to toxicity of the chemicals used. Mechanical methods, including aeration and mixing, are also available for the management of carbon dioxide, as well as dissolved oxygen, but these methods are highly energy consumptive.

Another persistent problem with aquafarming is slime formation, or pond scum. Slime formation in ponds is a result of the life processes of a variety of algae, fungi and fish. Areas in which slime has accumulated often produce foul odors, which can cause fish to acquire a malodor as well. Additionally, some organisms that produce the slime may also produce harmful by-products that could potentially lead to toxicity for fish or even consumers.

Further issues encountered in the aquaculture industry include the occurrence of infection and infestation in a fish population. All fish carry pathogens and parasites, and infectious diseases in fish often relate back to farmed and aquarium fish. Diseases are especially a factor in the mortality of young fish, and interacting factors can result in low grade infections becoming large scale epidemics, thus dramatically reducing the quality of fish and the possibility of commercial use.

Despite the reduction in quality of product, as well as growing environmental consequences of large-scale factory fish farming, the industry continues to grow extensively. Thus, there is a need for non-toxic and environmentally-friendly products for reducing the cost of feeding fish, as well as reducing the various issues contributing to high operating costs and reduced health and quality of fish products in aquaculture.

BRIEF SUMMARY OF THE INVENTION

The subject invention provides microbe-based products, as well as their use, for enhancing aquaculture. In particular, the subject invention provides materials and methods for producing healthy and high quality farmed fish. Advantageously, the present invention enhances aquaculture without use of, for example, toxic chemical compounds or antibiotics. Thus, the materials and methods of the subject invention are environmentally-friendly, operationally-friendly and cost-effective.

In one embodiment, the subject compositions and methods can be used for improving water quality and clarity, increasing pathogenic defense of fish and stimulating the growth of fish.

In one embodiment, the subject invention provides microbe-based compositions and methods of using these compositions for improving aquaculture and aquatic husbandry. In a specific embodiment, the subject invention utilizes compositions comprising biochemical-producing microorganisms, as well as by-products of their growth, such as biosurfactants, solvents and/or enzymes. In one embodiment, the composition comprises the fermentation broth resulting from the cultivation of the microorganism.

In preferred embodiments, the microbe of the subject compositions is a cultivated biosurfactant-, solvent- and/or enzyme-producing yeast. In one embodiment, the microbe is, for example, cultivated *Starmerella bombicola*, *Candida apicola*, *Wickerhamomyces anomalus*, *Pichia guilliermondii*, *Pichia occidentalis* and/or *Pseudozyma aphidis*. In one embodiment the microbe is a cultivated mutant of any of these species of yeast.

In preferred embodiments, the microbial growth by-product of the subject compositions is a biosurfactant, solvent, enzyme or other metabolite. In one embodiment, growth by-products produced by the microorganism work synergistically with one another to produce a desired effect.

In certain embodiments, the microbial growth by-product is present in the composition as a result of microbial growth. In some embodiments, a purified microbial growth by-product, e.g., one or more glycolipid and/or lipopeptide biosurfactants, can be added to the composition.

In one embodiment, the microbe-based composition according to the subject invention is obtained through cultivation processes ranging from small to large scale. The cultivation process can be, for example, submerged cultivation, solid state fermentation (SSF), and/or a combination thereof.

In certain embodiments, the compositions of the subject invention have advantages over, for example, biosurfactants, solvents and/or enzymes alone, including one or more of the following: high concentrations of mannoprotein as a part of a yeast cell wall's outer surface; the presence of beta-glucan in yeast cell walls; the presence of biosurfactants, metabolites and/or solvents (e.g., lactic acid, ethanol, ethyl acetate, etc.) in the culture.

In one embodiment the subject invention provides a method for enhancing aquaculture by applying a microbe-based composition comprising one or more strains of microorganism and/or microbial growth by-products to a fish farm. In one embodiment, the composition is a microbe-based composition of the subject invention.

"Enhancing aquaculture" according to the subject methods can mean, for example, improving the quality and clarity of fish farm water, e.g., by reducing carbon dioxide accumulation in water; preventing and/or treating infection or infestation by pathogenic agents present in a fish farm; and/or stimulating the growth of fish through feed supplementation and improved nutrient absorption.

In preferred embodiments, the microbes applied to the fish farm are cultivated biosurfactant-, solvent- and/or enzyme-producing yeasts, such as, for example, *Starmerella bombicola*, *Candida apicola*, *Wickerhamomyces anomalus*, *Pichia guilliermondii*, *Pichia occidentalis* and/or *Pseudozyma aphidis*. In one embodiment the microbe is a cultivated mutant of any of these species of yeast.

In certain embodiments, the microorganisms of the subject invention can be used in conjunction with other chemical and/or microbial treatments. For example, different species of yeasts can be used together, such as *Wickerhamomyces anomalus* and *Pseudozyma aphidis*. Other combinations of microorganisms are also envisioned.

The microbes can be either live (or viable) or inactive at the time of application. The methods of the subject invention can further comprise adding materials to enhance microbe growth during application (e.g., adding nutrients to promote microbial growth). In one embodiment, the nutrient sources can include, for example, organic sources of nitrogen and/or carbon.

In preferred embodiments, the microbial growth by-product according to the subject methods is a biosurfactant, solvent, enzyme or other metabolite. In one embodiment, growth by-products produced by the microorganism work synergistically with one another to produce a desired effect.

In certain embodiments, the microbial growth by-product is present as a result of microbial growth. In some embodiments, a purified microbial growth by-product, e.g., one or more glycolipid and/or lipopeptide biosurfactants, can be applied with the microbe-based composition.

In one embodiment, methods are provided for feeding fish using the microbe-based compositions of the subject invention. The microbe-based composition can serve as a highly nutritious supplemental food source for fish, as well as a preventative measure against contamination of fish food by pathogenic microorganisms. In one embodiment, the method of feeding fish can comprise introducing the microbe-based composition into a fish farm or an aquarium and allowing the fish therein to ingest the composition. Advantageously, the subject invention can be used to reduce the cost of feeding farmed fish.

Advantageously, the present invention can be used without releasing large quantities of inorganic compounds into the environment. Additionally, the compositions and methods utilize components that are biodegradable and toxicologically safe. Thus, the present invention can be used for enhancing fish farming as a "green" treatment.

DETAILED DESCRIPTION OF THE INVENTION

The subject invention provides microbe-based products, as well as their use, for enhancing aquaculture. In particular, the subject invention provides materials and methods for producing healthy and high quality farmed fish. Advantageously, the present invention enhances aquaculture without use of, for example, toxic chemical compounds or antibiotics. Thus, the materials and methods of the subject invention are environmentally-friendly, operational-friendly and cost-effective.

In certain embodiments, the subject invention enhances aquaculture through the treatment of fish farms and aquariums with a microbe-based composition capable of, for example, stimulating the growth of fish, improving water quality, and increasing pathogenic defense. In particular, compositions of the present invention can be used to, for example, feed fish and improve nutrient absorption in the digestive tract of fish, clean the water in fish ponds and tanks, protect fish from infections, and/or reduce carbon dioxide accumulation in water.

Selected Definitions

As used herein, "aquaculture," "aquafarming," "aquatic farming," "aquatic husbandry" or "fish farming" means the breeding, rearing, and harvesting of aquatic animals in a fish farm. Aquaculture can be intensive (relying on technology to raise fish in artificial enclosures at high densities) or extensive (performed in the ocean, or in natural and man-made lakes, bays rivers fiords, or other bodies of water). Aquaculture includes the production of seafood from hatchery fish and shellfish which are grown to market size in enclosures, ponds, tanks, aquariums, cages, or raceways. Additionally, aquaculture includes mariculture, which entails the culture of marine organisms in open seawater or enclosed sections of seawater. Furthermore, aquaculture includes stock restoration or "enhancement," wherein hatchery fish and shellfish are released into the wild in an effort to rebuild wild populations or coastal habitats. Even further, aquaculture includes the production of ornamental fish for the aquarium trade, as well as the husbandry of ornamental fish housed within aquariums. Species that can be farmed include freshwater or saltwater fish and shellfish, and can include ornamental fish, food fish, sport fish, bait fish, crustaceans, mollusks, algae, sea vegetables, or fish eggs.

As used herein, a "fish farm" is any water environment wherein aquaculture occurs or can occur. Fish farms according to this disclosure can include all types of water environments or sections of water environments, whether man-made or naturally occurring, including ponds, irrigation ditches, rivers, lakes, oceans, fiords, tanks, aquariums, cages, or raceways.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells may be absent, or present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more cells or propagules per milliliter of the composition.

As used herein, a propagule is any portion of a microorganism from which a new and/or mature organism can develop, including but not limited to, cells, conidia, cysts, spores (e.g., reproductive spores, endospores and exospores), mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of the microbe-based composition from a growth vessel.

As used herein, a "biofilm" is a complex aggregate of microorganisms, such as bacteria, wherein the cells adhere to each other. The cells in biofilms are physiologically distinct from planktonic cells of the same organism, which are single cells that can float or swim in liquid medium.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. As used herein, reference to "isolated" in the context of a microbial strain means that the strain is removed from the environment in which it exists in nature. Thus, the isolated strain may exist as, for example, a biologically pure culture, or as spores (or other forms of the strain) in association with a carrier. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight.

Purity is measured by any appropriate standard method, for example, by column chromatography, thin layer chromatography, or high-performance liquid chromatography (HPLC) analysis.

A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

As used herein, "modulate" is interchangeable with alter (e.g., increase or decrease). Such alterations are detected by standard art known methods such as those described herein.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" refers to a negative alteration of at least 1%, 5%, 10%, 25%, 50%, 75%, or 100%.

As used herein, "reference" refers to a standard or control condition.

As used herein, "surfactant" refers to a compound that lowers the surface tension (or interfacial tension) between two liquids or between a liquid and a solid. Surfactants act as detergents, wetting agents, emulsifiers, foaming agents, and dispersants. A "biosurfactant" is a surfactant produced by a living organism.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Microbe-Based Compositions

The subject invention provides microbes, as well as by-products of their growth, such as biosurfactants, solvents and/or enzymes. The subject invention also provides methods of using these microbes and their by-products in improved aquaculture and aquatic husbandry. Furthermore, the subject invention provides materials and methods of producing microbe-based compositions, as well as by-products of microbial growth.

Advantageously, the microbe-based compositions according to the subject invention are non-toxic (i.e., ingestion toxicity is more than 5 g/kg) and can be applied in high concentrations without causing irritation to, for example, skin. Thus, the subject invention is particularly useful where application of the microbe-based compositions occurs in the presence of living organisms, such as fish and shrimp produced for human consumption.

In one embodiment, the subject invention provides microbe-based compositions and methods of using these compositions for improving aquaculture and aquatic husbandry. In specific embodiment, the subject invention utilizes compositions comprising biochemical-producing microorganisms, as well as by-products of their growth, such as biosurfactants, solvents and/or enzymes. In one embodiment, the composition comprises the fermentation broth resulting from the cultivation of the microorganism.

In preferred embodiments, the microbe of the subject compositions is a cultivated biosurfactant-, solvent- and/or enzyme-producing yeast.

These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

Yeasts and fungi suitable for use according to the current invention, include, for example, *Candida* (e.g., *C. apicola*), *Saccharomyces* (e.g., *S. cerevisiae*, *S. boulardii sequela*, *S. torula*), *Issatchenkia*, *Kluyveromyces*, *Pichia*, *Wickerhamomyces* (e.g., *W. anomalus*), *Starmerella* (e.g., *S. bombicola*), *Mycorrhiza*, *Mortierella*, *Phycomyces*, *Blakeslea*, *Thraustochytrium*, *Phythium*, *Entomophthora*, *Aureobasidium pullulans*, *Pseudozyma aphidis*, *Aspergillus*, and/or *Rhizopus* spp.

In one embodiment, the microorganism is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Examples of killer yeasts according to the present invention include, but are not limited to, *Wickerhamomyces* (e.g., *W. anomalus*), *Pichia* (e.g., *P. anomala*, *P. guielliermondii*, *P. occidentalis*, *P. kudriavzevii*), *Hansenula*, *Saccharomyces*, *Hanseniaspora*, (e.g., *H. uvarum*), *Ustilago* (e.g., *U. maydis*), *Debaryomyces hansenii*, *Candida*, *Cryptococcus*, *Kluyveromyces*, *Torulopsis*, *Williopsis*, *Zygosaccharomyces* (e.g., *Z. bailii*), and others.

In one embodiment, the microbe is a cultivated killer yeast strain, or mutant thereof, such as *Wickerhamomyces anomalus* (*Pichia anomala*), *Pichia guielliermondii* and/or *Pichia occidentalis*.

In some embodiments, the microbe is a cultivated *Pseudozyma* yeast, for example, *Pseudozyma aphidis*. In other embodiments, the microbe is cultivated *Starmerella bombicola*. In yet another embodiment, the microbe is cultivated *Candida apicola*.

Other microbial strains including, for example, other microbial strains capable of accumulating significant amounts of, for example, biosurfactants, can also be used in accordance with the subject invention. Biosurfactants useful according to the present invention include glycolipids, mannoprotein, beta-glucan and other metabolites that have bioemulsifying and surface/interfacial tension-reducing properties.

In certain embodiments, the microorganisms of the subject invention can be used in conjunction with other chemical and/or microbial treatments. For example, different species of yeasts can be used together, such as *Wickerhamomyces anomalus* and *Pseudozyma aphidis*. Other combinations of microorganisms are also envisioned.

In preferred embodiments, the microbial growth by-product of the subject compositions is a biosurfactant, solvent, enzyme or other metabolite. Even more preferably, the microbial growth by-product is a biosurfactant. In one embodiment, the metabolites produced by the microorganism work synergistically with one another to produce a desired effect.

The microbes and microbe-based compositions of the subject invention have a number of beneficial properties that are useful for enhancing aquaculture. For example, biosurfactants produced according to the subject invention can inhibit microbial adhesion to a variety of surfaces, prevent the formation of biofilms, and can have powerful emulsifying and demulsifying properties. Additionally, biosurfactants are capable of reducing surface and interfacial tension of water in, for example, fish farms and aquariums.

In certain embodiments, the biosurfactants useful according to the subject invention are glycolipid biosurfactants, including mannosylerythritol lipids and sophorolipids. Mannosylerythritol lipids (MELs) are glycolipid biosurfactants abundantly produced by, for example, *Pseudozyma*. Sophorolipids (SLPs) are glycolipid biosurfactants produced by, for example, *Starmerella*, *Candida* and *Wickerhamomyces*.

MELs and SLPs exhibit excellent water surface and interfacial tension reduction properties, as well as versatile biochemical and physiological influences. For example, biosurfactants of the subject invention can have antifungal, antibacterial, anti-parasitic and antiviral properties. Furthermore, the subject biosurfactants exhibit highly effective emulsifying and demulsifying properties.

Further components can be added to the microbe-based composition, for example, buffering agents, carriers, other microbe-based compositions produced at the same or different facility, viscosity modifiers, preservatives, nutrients for microbe growth, tracking agents, biocide, other microbes, surfactants, emulsifying agents, lubricants, solubility controlling agents, pH adjusting agents, preservatives, stabilizers and ultra-violet light resistant agents.

In certain embodiments, the microbe-based composition of the subject invention further comprises a carrier. The carrier may be any suitable carrier known in the art that permits the yeasts or yeast by-products to be delivered to target waters, surfaces and/or fish, etc. in a manner such that the product remains viable, or, in the case of inactive yeast, retains the components necessary to be effective.

In one embodiment, the composition can further comprise buffering agents, including organic and amino acids or their salts, to stabilize pH near a preferred value. Suitable buffers include, but are not limited to, citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and mixtures thereof. Phosphoric and phosphorous acids or their salts may also be used. Synthetic buffers are suitable to be used but it is preferable to use natural buffers such as organic and amino acids or their salts.

In a further embodiment, pH adjusting agents include potassium hydroxide, ammonium hydroxide, potassium carbonate or bicarbonate, hydrochloric acid, nitric acid, sulfuric acid and mixtures thereof.

The pH of the microbe-based composition should be suitable for the microorganism of interest. In a preferred embodiment, the pH of the final microbe-based composition ranges from 6.5-7.5.

In one embodiment, additional components such as an aqueous preparation of a salt, such as sodium bicarbonate or carbonate, sodium sulfate, sodium phosphate, or sodium biphosphate, can be included in the microbe-based composition.

Optionally, the composition can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In one embodiment, the microbe-based composition according to the subject invention is obtained through known cultivation processes ranging from small to large scale. The cultivation process can be, for example, submerged cultivation, solid state fermentation (SSF), and/or a combination thereof.

The product of fermentation may be used directly without extraction or purification. If desired, extraction and purification can be easily achieved using standard extraction methods or techniques known to those skilled in the art. In certain embodiments, the microbe-based composition of the subject invention can comprise the fermentation broth containing a live and/or an inactive culture and/or the microbial metabolites produced by the microorganism and/or any residual nutrients.

The composition may be, for example, at least, by weight, 1%, 5%, 10%, 25%, 50%, 75%, or 100% broth. The amount of biomass in the composition, by weight, may be, for example, anywhere from 0% to 100% inclusive of all percentages therebetween.

The biomass content of the fermentation broth may be, for example from 5 g/l to 180 g/l or more. In one embodiment, the solids content of the broth is from 10 g/l to 150 g/l.

In certain embodiments, the compositions of the subject invention have advantages over, for example, biosurfactants, solvents and/or enzymes alone, including one or more of the following: high concentrations of mannoprotein as a part of a yeast cell wall's outer surface; the presence of beta-glucan in yeast cell walls; the presence of biosurfactants, metabolites and/or solvents (e.g., lactic acid, ethanol, ethyl acetate, etc.) in the culture.

The microorganisms in the microbe-based composition may be in an active or inactive form. The microbe-based product composition may contain a combination of active and inactive microorganisms.

The microbe-based compositions may be used without further stabilization, preservation, and storage. Advantageously, direct usage of these microbe-based compositions reduces the possibility of contamination from foreign agents and undesirable microorganisms, and maintains the activity of the by-products of microbial growth.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and combination thereof.

As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method of cultivation can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics can be used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. The cultivation may be carried out continuously at a constant pH, or the cultivation may be subject to changing pH.

When metal ions are present in high concentrations, use of a chelating agent in the liquid medium may be necessary.

The method and equipment for cultivation of microorganisms and production of the microbial by-products can be performed in a batch, a quasi-continuous process, or a continuous process.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In other embodiments, the cultivation system may be self-sterilizing, meaning the organism being cultivated is capable of preventing contamination from other organisms due to production of antimicrobial growth by-products or metabolites.

The biomass content of the fermentation broth may be, for example, from 5 g/l to 180 g/l or more. In one embodiment, the solids content of the broth is from 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of the microbial growth by-product.

In one embodiment, the method for producing a microorganism further comprises inactivating the microorganism for use in a microbe-based composition of the subject invention. Preferably, inactivation is carried out using methods that do not result in denaturation of the desirable components of the microorganism's cell wall, etc.

In one embodiment, biosurfactants are produced by cultivating a microbe strain of the subject invention under conditions appropriate for growth and biosurfactant production; and, optimally, purifying the biosurfactant. Enzymes or other proteins can also be produced by cultivating a microbe strain of the subject invention under conditions appropriate for growth and enzyme/protein expression; and, optimally, purifying the enzyme or other protein.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or can contain cells. In this manner, a quasi-continuous system is created.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form. The microbe-based products may contain combinations of active and inactive microorganisms. Preferably, the microorganisms are inactivated.

The microbe-based products may be used without further stabilization, preservation, and storage. Advantageously, direct usage of these microbe-based products reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use. In another embodiment, the microbes can be inactivated prior to use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

In certain embodiments, biosurfactants can be added to the microbe-based composition. In preferred embodiments, the biosurfactants are in a purified form.

Biosurfactants are a structurally diverse group of surface-active substances produced by microorganisms. Biosurfactants are biodegradable and can be easily and cheaply produced using selected organisms on renewable substrates. All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces.

Biosurfactants include low molecular weight glycolipids (e.g., rhamnolipids, sophorolipids, mannosylerythritol lipids), lipopeptides (e.g., surfactin, iturin, fengycin), flavolipids, phospholipids, and high molecular weight polymers such as lipoproteins, lipopolysaccharide-protein complexes, and polysaccharide-protein-fatty acid complexes. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Biosurfactants accumulate at interfaces, thus reducing interfacial tension and leading to the formation of aggregated micellular structures in solution. Safe, effective microbial biosurfactants reduce the surface and interfacial tensions between the molecules of liquids, solids, and gases. The ability of biosurfactants to form pores and destabilize biological membranes permits their use as antibacterial, antifungal, and hemolytic agents. Combined with the characteristics of low toxicity and biodegradability, biosurfactants are advantageous for use aquaculture industry for a wide variety of applications.

In one embodiment, the biosurfactants that can be used according to the subject invention include one or more glycolipids and/or lipopeptides. In one embodiment, the glycolipids are selected from rhamnolipids (RLP), sophorolipids (SLP), trehalose lipids and mannosylerythritol lipids (MEL). In one embodiment, the lipopeptides are selected from surfactin, iturin A, and fengycin.

In preferred embodiments, a combination of any of these biosurfactants can be applied with the microbe-based composition. Preferably, the total concentration of biosurfactant in the composition does not exceed 5 g/kg. In certain embodiments, the concentration of biosurfactant ranges from 0.05% to 90% of the total composition by weight, preferably 0.1% to 50%, more preferably 0.5% to 2%.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In one embodiment, different microbe strains are cultured in different tanks for the purpose of producing an inactive microbe-based composition. The composition is prepared by inactivation of the culture at pasteurization temperature (up to 65 to 70° C. for a time period sufficient to inactivate 100% of the yeast cells) and increasing pH value up to about 10.0-12.0. This induces partial hydrolysis of cells and allows for freeing of some nutritional components therein. Then, the composition is neutralized to a pH of about 6.5-7.5 and the various components of hydrolysis are mixed. The resulting microbe-based product can then be used for fish feed and water treatment.

Methods of Enhancing Aquaculture Using Compositions of the Subject Invention

In certain embodiments, the subject invention provides environmentally-friendly, cost-efficient materials and methods for enhancing aquaculture. In specific embodiments, the present invention provides methods for improving the health and quality of fish cultivated in fish farms. In another embodiment, methods are provided for feeding fish cultivated in fish farms.

As used herein, "applying" a composition or product, or "treating" a fish farm refers to contacting a composition or product with a target or site such that the composition or product can have an effect on that target or site. The effect can be due to, for example, microbial growth and/or the action of a biosurfactant or other growth by-product. According to the present invention, application or treatment can be achieved by, for example, piping, pumping or pouring a composition into the water environment contained within a fish farm, or by, for example, coating or spreading a composition onto the various surfaces, walls, or enclosures of a fish farm.

In one embodiment, methods are provided for enhancing aquaculture by applying to a fish farm or an aquarium a microbe-based composition comprising one or more strains of microorganisms and/or microbial growth by-products. The method optionally includes adding organic sources of nutrients, e.g., carbon or nitrogen, and/or other agents to the site in order to promote microbial growth (if active microbes are used).

As used herein, "improving" or "enhancing" aquaculture means improving the health and quality of fish cultivated in fish farms. Aquaculture enhancement can be achieved indirectly, for example, by improving the quality of the environment in which the fish are produced, or directly, for example, by providing nutritional and health benefits to the fish themselves.

The subject methods and compositions are capable of, for example, improving water quality and clarity, increasing pathogenic defense and stimulating the growth of fish. In particular, compositions of the present invention can be used to clean water and surfaces within fish ponds and tanks, protect fish from infection or infestation, reduce carbon dioxide accumulation in water, or feed fish and improve nutrient absorption.

In certain embodiments, the subject invention provides methods of enhancing aquaculture by removing slime, or pond scum, that has accumulated in a fish farm or aquarium as a result of, for example, algal growth. The microbe-based composition of the subject invention can be applied to, for example, the water, floors, walls, or other surfaces of fish ponds, tanks, or aquariums. In one embodiment, the composition acts as a biological de-emulsifier capable of dispersing the slime components and/or killing the organism that comprises the slime.

Pond slime or scum is generally the result of the growth of algae in a body of water. Algae are aquatic organisms that are naturally occurring and abundant in nature. These complex organisms are troublesome for many lakes, ponds, lagoons and wastewater treatment systems, as they can multiply and potentially take over an entire water source in the form of a slimy, often foul-smelling mat or coating in, or on the surface of, the water. Often, algal blooms will deplete the oxygen in a water source, which can result in fish die-offs. Some blooms, for example blue-green algal blooms (cyanobacteria), can also be harmful for humans and aquatic organisms due to the toxic by-products they produce.

Types of pond scum-forming algae that can be effectively controlled using the present invention include, but are not limited to, planktonic algae (e.g., *Anabaena, Chlorella, Pediastrum, Scenedesmus* and *Oocystis*), filamentous algae (e.g., *Spirogyra, Cladophora, Rhizoclonium, Mougeolia, Zygnema* and *Hydrodictyon*), and others, such as *Lyngbya, Pithophora*, toxic bloom-forming algae, or colonial diatoms.

In some embodiments, the subject invention provides methods of enhancing aquaculture by improving the overall quality of fish farm water. In one embodiment, improving water quality means reducing the amount of carbon dioxide in fish farm water. In another embodiment, improving water quality means reducing the amount of hydrogen sulfide in fish farm water. In yet another embodiment, improving water quality means increasing and/or balancing oxygen levels in fish farm water.

Particularly in high pressure, high volume aquaculture operations, where fish farms are crowded, the gaseous contents of the water can become imbalanced, thus leading to unhealthy living conditions for the fish. For example, fish in crowded ponds can experience oxygen depletion due to the large population size. This can lead to increases in carbon dioxide content, which leads to fish asphyxiation and mortality.

Additionally, the formation of pond sludge at the bottom of fish farms can lead to depleted oxygen levels, as well as increased hydrogen sulfide levels in the water. Pond sludge forms as a result of various organic materials settling to the bottom, for example, dead algae, bacteria, fish waste and dirt. Pond sludge is typically impenetrable to oxygen, thus promoting the growth of hydrogen sulfide-producing anaerobic bacteria. Hydrogen sulfide is toxic to other organisms, and also produces a strong, rotten egg smell. Thus, removal of hydrogen sulfide and its source is imperative for the health of farmed fish.

In certain embodiments, the reduction of carbon dioxide and/or hydrogen sulfide using the subject invention allows for increased oxygen levels in fish farm water, and thus enhanced water quality and fish quality. In some embodiments, however, if additional oxygenation of the water is desired, the method can further comprise applying a means of oxygenation to the water, for example, using filters, aerators, pumps, and/or other known means for aerating water.

In some embodiments, the subject invention provides methods of enhancing aquaculture by reducing carbon dioxide and/or hydrogen sulfide concentration within the water of a fish farm. The microbe-based composition of the subject invention can be applied to the water, where it acts to reduce the interfacial tension of the water, thus helping in the release of carbon dioxide and/or hydrogen sulfide entrapped in the water.

In specific embodiments, the reduction of carbon dioxide enhances aquaculture by preventing fish mortality due to carbon dioxide asphyxiation.

In other embodiments, the subject invention provides methods of enhancing aquaculture by preventing hydrogen sulfide formation within the water of a fish farm. The microbe-based composition of the subjection invention can be applied to the water or to the bottom of a fish pond, where its acts to demulsify pond sludge where anaerobic, hydrogen sulfide-producing bacteria thrive. In further embodiments, the composition can act to control the anaerobic bacteria that produce the hydrogen sulfide due to the antimicrobial properties of the composition.

In specific embodiments, the reduction of hydrogen sulfide, and/or the prevention of its formation enhance aquaculture by preventing fish mortality due to the toxic effects of hydrogen sulfide buildup.

In some embodiments, the subject invention provides methods of enhancing aquaculture by preventing the spread of infection within a fish farm population. Additionally, the subject invention can be used to prevent infestations of pathogens and parasites, such as Helminths. The microbe-based composition of the subject invention can be applied, for example, to the water or surfaces within a fish farm, where the composition's antibacterial, antifungal, antiviral, anti-parasitic and anti-adhesive properties prevent fish from becoming inoculated with a variety of diseases known to cause fish illness or mortality, as well as prevent infestations of disease-causing organisms within the environment of the fish farm.

Examples of pathogens against which the subject methods and compositions are useful include, but are not limited to, viruses (e.g., *Aquabirnavirus, Betanodavirus, Orthomyxovirus, Alphavirus*, rhabdoviruses, and *Ranavirus*), bacteria (e.g., *Pseudomonas fluorescens, Aeromonas, Edwardsiella, Flavobacterium, Francisella, Photobacterium, Piscirickett-*

*sia, Pseudomonas, Tenacibaculum, Vibrio, Yersinia, Lactococcus, Renibacterium* and *Streptococcus*), fungi (e.g., *Saprolegnia, Aspergillus, Penicillium, Exophiala, Ichthyophonus, Branchiomyces, Dermocystidium, Prototheca, Oscillatoria, Phoma herbarum,* and *Paecilomyces*), water molds (e.g., *Saprolegnia* sp.), and parasites (e.g., nematodes, tapeworms, roundworms, leeches, lice, metazoan parasites such as copepods, unicellular parasites, such as *Ichthyophthirius multifiliis*, and helminths such as *Eustrongylides*).

Viral diseases that can be mitigated or prevented using the subject invention include, but are not limited to, infectious pancreatic necrosis, viral nervous necrosis, salmon anemia virus, pancreatic disease, infectious hematopoietic necrosis virus, viral hemorrhagic septicemia virus, and epizootic hematopoietic necrosis virus), Bacterial diseases that can be mitigated or prevented using the subject invention include, but are not limited to fin rot, fish dropsy, motile aeromonads septicaemia, furunculosis, chryseobacteriosis, enteric septicaemia of catfish, edwardsiellosis or putrefactive disease, *columnaris*, false *columnaris*, flavobacteriosis or rainbow trout fry syndrome, bacterial gill disease, francisellosis, winter ulcer disease, pasteurellosis, piscirickettsiosis or rickettsial septicaemia, pseudomonads septicaemia or red spot disease, tenacibaculosis, vibrosis, yersiniosis or enteric redmouth disease, lactococcosis, nocardiosis, bacterial kidney disease, staphylococcosis, streptococcosis, and haemorrhagic septicaemia.

Other diseases or infestations that can be mitigated or prevented using the subject invention include gill rot, *Ichthyophonus* disease, saprolegniasis, velvet disease, hole in the head, and whirling disease. Advantageously, the methods improve pathogenic defense of farmed fish without use of harsh chemicals or antibiotics.

In some embodiments, the subject invention provides methods of enhancing aquaculture by improving nutrient absorption in the digestive tracts of farmed fish. Specifically, when ingested by fish, the biosurfactants in the microbe-based composition of the subject invention contribute to increased overall health and quality of farmed fish by improving the absorption (i.e., the bioavailability) of nutrients, including fat-soluble vitamins, within the digestive tracts of the fish.

The composition can be applied to fish farm water in the form of, for example, a liquid solution, or as dry powder, meal, flakes, granules or pellets. Fish that ingest the subject compositions can experience increased weight gain when compared to fish fed with conventional fishmeals, with most of the weight gain a result of increased body protein percentage accompanied by lower body fat percentage.

In another embodiment, the subject invention provides methods of supplementing the feeding of fish, as well as methods of lowering the cost of feeding fish. The microbe-based composition of the subject invention can be applied to fish farm water as a single cell protein source comprising yeast cells and optionally, purified biosurfactants. Yeast cells can provide an abundance of, for example, proteins, carbohydrates, lipids, fatty acids, minerals and vitamins in concentrated amounts.

In certain embodiments, the composition is formulated as granules, which can be fed to fish alongside granules of traditional fish meal. In some embodiments, the composition is combined with the ingredients of traditional fish meal, and the combination is used to make granules. In yet other embodiments, the composition is fed to fish on its own, in place of traditional fish meal. Advantageously, in addition to increasing the nutrient absorption of fish, the subject compositions are capable of preventing the contamination of fish feed by viral, fungal and bacterial agents due to the composition's antimicrobial properties.

Due to the growing costs of traditional fish- and fish oil-derived feeds, many aquaculture operations have begun to utilize grain-based feed for feeding fish. Ingredients such as corn, soy, and sorghum are now being used to manufacture fish feed. The effects on the health of fish themselves from grain-based diets are not conclusively known, but nonetheless have potential to be undesirable overtime.

Additionally, the success of, for example, the seafood industry relies in part on the attractive health benefits of human consumption of seafood, such as high levels of Omega-3 fatty acids. By transitioning farmed fish from carnivorous or omnivorous diets to strictly plant-based diets, the nutritional content of the final fish product can be altered, for example, the fatty-acid content of fish products may be reduced. The effects of such a change on the seafood industry, as well as on human nutrition, could be extensive.

Thus, by acting as a supplement to existing fish feeds, the subject invention can be used to mitigate the increasing costs of using traditional fish-based fish feeds. The subject invention can lower the cost of feeding fish, while allowing for a return to traditional fish-based feeds, all without compromising the health and quality of farmed fish.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a fish farm). For example, the microbe growth facility may be less than 300, 250, 200, 150, 100, 75, 50, 25, 15, 10, 5, 3, or 1 mile from the location of use.

Because the microbe-based product is generated on-site or near the site of application, without the requirement of stabilization, preservation, prolonged storage and extensive transportation processes of conventional production, a much higher density of live microorganisms can be generated, thereby requiring a much smaller volume of the microbe-based product for use in an on-site application. This allows for a scaled-down bioreactor (e.g., smaller fermentation tank; smaller supplies of starter material, nutrients, pH control agents, and de-foaming agent, etc.), which makes the system efficient. Furthermore, local production facilitates the portability of the product.

Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization or have sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the broth in which the microbes are grown. If desired, the compositions can have a high density of vegetative cells, inactivated cells, or a mixture of vegetative cells, inactivated cells, reproductive spores, mycelia and/or other microbial propagules. Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell- and/or propagule-count product and the associated broth and metabolites in which the microbes are originally grown.

Advantageously, in preferred embodiments, the systems of the subject invention harness the power of naturally-occurring local microorganisms and their metabolic by-products to treat plant pathogenic bacteria. Local microbes can be identified based on, for example, salt tolerance, ability to grow at high temperatures, and the use of genetic identification of sequences. Additionally, the microbe growth facilities provide manufacturing versatility by their ability to tailor the microbe-based products to improve synergies with destination geographies.

The cultivation time for the individual vessels may be, for example, from 1 day to 2 weeks or longer. The cultivation product can be harvested in any of a number of different ways.

Local production and delivery within, for example, 24 hours of fermentation results in pure, high microbe density compositions and substantially lower shipping costs. Given the prospects for rapid advancement in the development of more effective and powerful microbial inoculants, consumers will benefit greatly from this ability to rapidly deliver microbe-based products.

The microbe-based products of the subject invention can be used in a variety of unique settings because of, for example, the ability to efficiently deliver: 1) fresh fermentation broth with active metabolites; 2) a mixture of microbes and fermentation broth; 3) a composition with live cells, or spores, mycelia, conidia or other microbial propagules; 4) compositions with a high density of microbes, including live cells and/or spores, mycelia, conidia or other microbial propagules; 5) microbe-based products on short-order; and 6) microbe-based products in remote locations.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

EXAMPLES

Example 1—Cultivation of *Wickerhamomyces anomalus* and *Pseudozyma aphidis*

*Wickerhamomyces anomalus* yeast is grown in a reactor with working volume of 800 L for biomass and sophorolipid production in non-sterilized conditions. A method of empty vessel sanitation is used wherein internal surfaces are treated with 2-3% hydrogen peroxide and rinsed with bleach and high pressure hot water. The culture medium components containing all necessary components are temperature decontaminated at 85-90° C. or dissolved in 3% hydrogen peroxide. The fermentation temperature is kept between 25-30° C. The pH begins at 5.0-5.5, and then decreases to 3.0-3.5, where it is stabilized. Production of biomass is achieved in about 48 hours of fermentation.

Accumulation of sophorolipids can occur after 7 to 9 days of fermentation. Upon completion of the fermentation, the culture containing biomass and, if applicable, low concentration of sophorolipid, can then be applied to, for example, fish ponds or tanks containing fish.

*Pseudozyma aphidis* is grown in the same reactors under the same conditions, with two exceptions: optimal pH is kept between 5.0-5.5, and production of biomass and mannosylerythritol lipids (MELs) is achieved in 7 to 12 days.

Example 2—Composition for Feeding Fish and Treatment of Fish Farms

Both a treatment and feed product are obtained using a medium containing glucose, canola oil, yeast extract, $NH_4Cl$, $KH_2PO_4 \cdot H_2O$ and $MgSO_4 \cdot 7H_2O$. The initial pH is adjusted to about 5.5 with KOH. The cultures are grown at about 25° C. with no stabilization.

*Wickerhamomyces anomalus* and *Pseudozyma aphidis* are cultured in different tanks. After completion of the fermentation process, the composition is prepared by inactivation of the culture at pasteurization temperature (up to 65 to 70° C. for a time period sufficient to inactivate 100% of the yeast cells) and increasing pH value up to about 10.0-12.0. This induces partial hydrolysis of cells and allows for freeing of some nutritional components therein. Then, the composition is neutralized to a pH of about 6.5-7.5 and the various components of hydrolysis are mixed.

The resulting microbe-based product can be used for fish feed and water treatment.

Example 3—Fish Food

It is possible to replace a significant part, or the entirety, of a fish's diet with a composition of the subject invention. In one embodiment, a composition comprising yeast biomass (e.g., *W. anomalus, P. aphidis, S. bombicola* and/or *C. apicola*) and optionally, purified biosurfactants, can be dried using air heated to 100-150° C. to produce fish feed granules. The granules can be mixed with traditional fish meal in a ratio of, for example, 1:1, 2:1, or 1:2. The granules can also be used to replace the traditional fish meal altogether, if desired. The subject yeast- and biosurfactant-based food composition prevents contamination of food from microbial pathogens, as well as subsequent potential illness to fish who ingest the food. The composition can also increase the bioavailability of nutrients to fish who ingest it, thus leading to overall healthier fish.

A diet comprising 50% yeast single cell protein in place of fishmeal gives optimal growth responses in terms of percentage weight gain. Proximate examination of a carcass composition of a whole fish body shows that a fish fed with 50% yeast single cell protein has higher percentage of body protein and with a lower amount of fat versus fish fed with traditional feed.

We claim:

1. A method of reducing carbon dioxide and/or hydrogen sulfide in fish farm water, which comprises applying a composition comprising a first yeast culture comprising cells of an inactivated *Starmerella bombicola* yeast and a sophorolipid (SLP) and a second yeast culture comprising cells of an inactivated *Pseudozyma aphidis* yeast and a mannosylerythritol lipid (MEL), to the fish farm water, said composition comprising no living yeast cells, wherein the *Starmerella bombicola* yeast of the first yeast culture and the *Pseudozyma aphidis* yeast of the second yeast culture are inactivated via pasteurization;

wherein said reduction in carbon dioxide and/or hydrogen sulfide results in one or more of the following:

reduced carbon dioxide asphyxiation in fish growing in the fish farm water;

reduced hydrogen sulfide toxicity in the fish; and/or increased oxygen levels in the fish farm water.

2. The method of claim 1, wherein the fish farm is a pond, lake, ocean, fiord, raceway, river, aquarium, tank or cage.

3. The method of claim 1, comprising measuring a level of hydrogen sulfide in the fish farm water.

* * * * *